United States Patent
Alharthy et al.

(10) Patent No.: US 11,726,033 B1
(45) Date of Patent: Aug. 15, 2023

(54) DETERMINATION OF TOTAL CRUDE OIL IN WATER BY ABSORBANCE SPECTROPHOTOMETRY

(71) Applicant: Saudi Arabian Oil Company, Dhahran (SA)

(72) Inventors: Mohammad Alharthy, Al-Khobar (SA); Osama Alzahrani, Dammam (SA); Nada Alghamdi, Dharan (SA); NagoorPitchal MeeranPillai, Al-Khobar (SA); Ali Almuhaimeed, Al-Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/682,243

(22) Filed: Feb. 28, 2022

(51) Int. Cl.
*G01N 21/33* (2006.01)
*G01N 33/18* (2006.01)
*G01N 1/40* (2006.01)

(52) U.S. Cl.
CPC ........... *G01N 21/33* (2013.01); *G01N 1/4077* (2013.01); *G01N 33/1833* (2013.01); *G01N 2001/4083* (2013.01); *G01N 2201/127* (2013.01); *G01N 2201/12746* (2013.01)

(58) Field of Classification Search
CPC .. G01N 21/33; G01N 1/4077; G01N 33/1833; G01N 2001/4083; G01N 2201/127; G01N 2201/12746
See application file for complete search history.

(56) References Cited

U.S. PATENT DOCUMENTS

| | | | |
|---|---|---|---|
| 5,381,002 A | 1/1995 | Morrow et al. | |
| 6,117,682 A | 9/2000 | Lynn et al. | |
| 9,297,747 B2 | 3/2016 | Han et al. | |
| 2010/0231904 A1 | 9/2010 | Tyrie et al. | |
| 2011/0151576 A1* | 6/2011 | Perfect | G01N 33/2823 252/301.16 |
| 2012/0170023 A1* | 7/2012 | Szobota | G01N 21/552 356/51 |
| 2013/0124106 A1* | 5/2013 | Rogel | G01N 33/2823 73/61.55 |
| 2014/0260561 A1 | 9/2014 | Brost et al. | |
| 2020/0033315 A1* | 1/2020 | Cao | G01N 33/287 |
| 2021/0102932 A1* | 4/2021 | Locklear | G01N 33/287 |

OTHER PUBLICATIONS

Leong et al., "UV-Vis Spectroscopy: A new approach for assessing the color index of transformer insulating oil," Sensors, vol. 18, No. 2175, 15 pages. (Year: 2018).*

(Continued)

*Primary Examiner* — Kiho Kim
(74) *Attorney, Agent, or Firm* — Fish & Richardson P.C.

(57) ABSTRACT

A method for quantifying a crude oil in water is provided. The method includes selecting an ultraviolet/visible (UV/Vis) wavelength to perform a measurement, preparing calibration solutions in xylene, and preparing a calibration curve from the calibration solutions. A sample is prepared including extracting the crude oil from the water in a two-phase separation with xylene. An absorbance of the sample in the xylene is measured at the UV/Vis wavelength. A concentration of the crude oil in the water is calculated from the absorbance.

11 Claims, 8 Drawing Sheets

(56) References Cited

OTHER PUBLICATIONS

Banda-Cruz et al., "Crude oil UV spectroscopy and light scattering characterization," Petroleum Science and Technology, Jun. 2016, 34(8):732-738.

Bastow et al., "Ultraviolet spectroscopy for the analysis of oil-in-water effluent using isopropanol as co-solvent," Applied Spectroscopy, 1997, 51(3):318-322.

spectrosci.com [online], "Techniques for measuring oil in water," 2016, retried on Dec. 17, 2021 from URL <https://www.spectrosci.com/knowledge-center/resource-library/oil-in-water-and-soil>, 5 pages.

* cited by examiner

_US 11,726,033 B1_

DETERMINATION OF TOTAL CRUDE OIL IN WATER BY ABSORBANCE SPECTROPHOTOMETRY

TECHNICAL FIELD

The present disclosure is directed to a method for the quantitative determination of total crude oil in water by absorbance spectrophotometry.

BACKGROUND

The production of crude oil often produces entrained water, termed a water-cut. As reservoirs age, the water-cut increases. Generally, the entrained water is separated from the oil, and treated in a water oil separation plant (WOSP) to separate dispersed oily materials (emulsified oil) from the produced water, so that it may be injected into disposal wells or used for other applications. The basic design of the WOSP was intended to handle water-cuts less than 10%.

However, as an oil field matures, oil production decreases while water production increases. The current water/oil ratio is estimated at 2:1 to 3:1 worldwide, converting to a water cut of 50% to 75% of the total amount of produced fluids. A higher water-cut causes a significant reduction of separation efficiency, as the water requires more retention time in a WOSP for complete separation. An extreme volume of emulsified water can exceed the processing capacity of the WOSP, resulting in incomplete oil water separation. This leads to poor quality, or offspec, water being provided to injection wells. Accordingly, determining the amount of oil in wastewater streams is important for determining the operations needed for purification prior to disposal.

SUMMARY

An embodiment described in examples herein provides a method for quantifying a crude oil in water. The method includes selecting a ultraviolet/visible (UV/Vis) wavelength to perform a measurement, preparing calibration solutions in xylene, and preparing a calibration curve from the calibration solutions. A sample is prepared including extracting the crude oil from the water in a two-phase separation with xylene. An absorbance of the sample in the xylene is measured at the UV/Vis wavelength. A concentration of the crude oil in the water is calculated from the absorbance.

DETAILED DESCRIPTION

A method is provided for the quantitative determination of crude oil in water by UV-visible spectrophotometry. A corresponding crude oil sample is analyzed by the spectrophotometer at a range of wavelength values to determine the wavelength value that will be used in calibration and sample measurement. Then, an oil-soluble solvent, xylene, is introduced to the water samples for liquid-liquid extraction (LLE). The organic layer is then separated from water. The concentration of total crude oil in the organic layer is determined by external calibration in the ppm level using UV-Visible spectrophotometry at the chosen wavelength value. Subsequently, the concentration of total crude oil in water is calculated.

Figure 1:
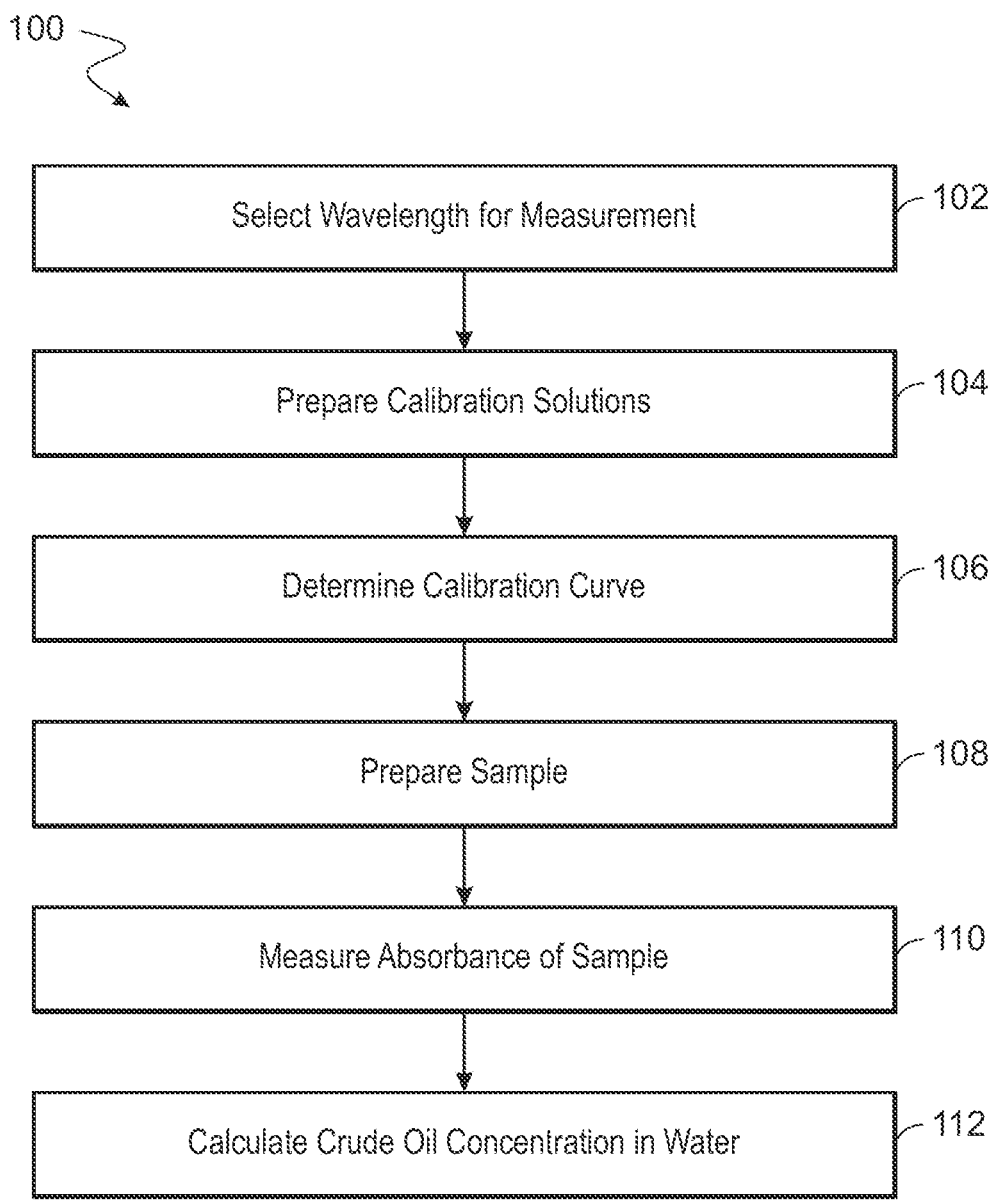
FIG. 1 is a process flow diagram of a method for determining total crude oil in water by absorbance spectroscopy spectrophotometry.

FIG. 1 is a process flow diagram of a method 100 for determining total crude oil in water by absorbance spectroscopy spectrophotometry. The method 100 begins at block 102 with selecting a wavelength in the UV-Visible spectrum for the measurement. As different crude oil samples have different compositions, selecting an appropriate wavelength will increase both the accuracy and the precision of the measurement. A corresponding crude oil sample is analyzed by the spectrophotometer at a range of wavelength values to determine the wavelength value that will be used in calibration and sample measurement. The selection of the wavelength is discussed further with respect to FIGS. 2-4 of the examples.

At block 104, calibration solutions are mixed in xylene at a number of concentrations. The concentrations may be selected to cover the expected range of oil concentrations. At block 106, the calibration solutions are used to determine a calibration curve. The mixing of the calibration solutions and the determination of the calibration curve are discussed further with respect to FIGS. 5-7 of the examples.

At block 108, the sample is prepared for measurement. An oil-soluble solvent, xylene, is introduced to the water samples for liquid-liquid extraction (LLE), for example, in a separatory funnel. The organic layer is then separated from water and centrifuged to remove solid impurities and water droplets. At block 110, the absorbance of the sample is measured at the selected wavelength. At block 112, the concentration of total crude oil in the organic layer is determined by from the calibration curves and the absorbance of the sample. The measurement of the absorbance of the sample and the calculation of the crude oil concentration are discussed further with respect to FIG. 8 of the example.

Examples

Instrumentation

The method 100 described herein uses the following equipment (or equivalent). Weights are measured on a calibrated analytical balance capable of weighing up to 0.1 mg, for example, a Mettler model AT-261 available from Mettler-Toledo of Columbus, Ohio, USA. The centrifuge used for the purification of the oil sample after extraction can be a Seta Oil Test Centrifuge 90000-0 (operating range: 300-2800 rpm) available from Stanhope-Seta of Chertsey, Surrey, UK. The spectrophotometer used for the UV-Vis measurements was a Jenway 6300 UV-Vis Spectrophotometer available from Cole-Parmer of Stone, Staffordshire, UK.

Materials and Reagents

Lab Equipment

The lab equipment used for the method 100 includes a 500 mL separatory funnel, 15 mL glass test tubes, 10 mL volumetric flasks, 50 mL volumetric flasks, adjustable volume pipettes, and a spectrophotometer cuvette. Disposable pipette tips were also used. As some measurements may be made in the ultraviolet range, the cuvette may be a 1 cm×1 cm quartz cuvette.

Chemicals

The chemicals used in the method 100 includes xylene, purity ≥98.5%, sodium chloride, purity ≥99.6%, and calcium chloride dihydrate, purity ≥99.0%. A corresponding crude oil sample from the same source of the crude oil in the water samples is used to select the measurement wavelength and prepare the calibration samples. In this example described herein, two crude oil samples were used to demonstrate the techniques, termed crude oil A and crude oil B, herein.

Select Wavelength for Measurement

Figure 2:
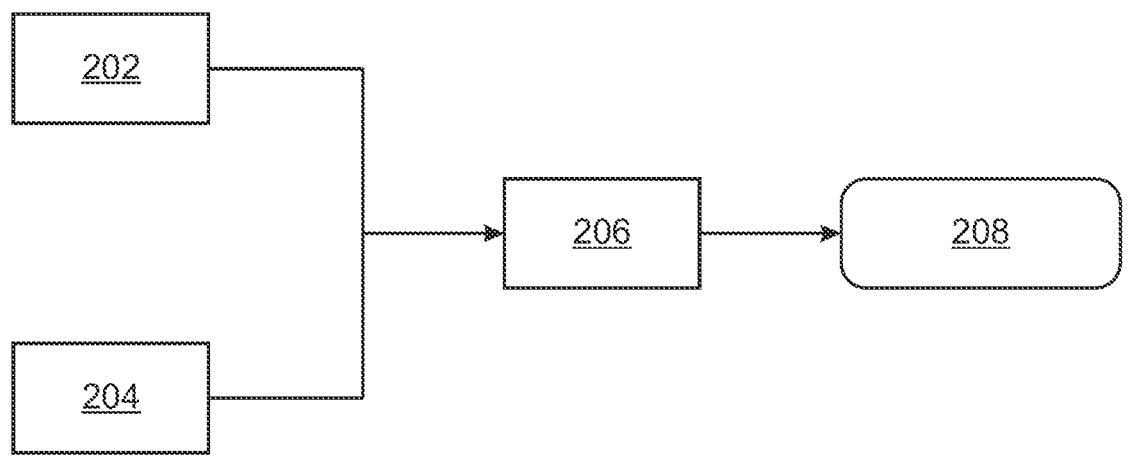
FIG. 2 is a schematic diagram of the wavelength selection process.

FIG. 2 is a schematic diagram of the wavelength selection process. This may correspond to block 102 of the method 100 of FIG. 1. In FIG. 2, the corresponding crude oil 202 and xylene tool for were combined to form the solution 206 of crude oil in xylene. The solution 206 were measured in the spectrophotometer 208 to generate a number of values of absorbance at different wavelengths. In some embodiments, a scanning spectrophotometer may be used to generate a spectrum.

The spectrophotometer was powered and allowed to warm until the absorbance (or any other reading, such as % T or CONC) reading was stable.

As described above, the corresponding crude oil 202 was taken from the same source of crude oil as would be present in the water samples. 0.001 g of the corresponding crude oil was added to in a 10 mL volumetric flask and diluted to the mark with xylene. The flask was shaken to prepare a 100 ppm solution (other concentrations can be used).

ABS (absorbance) was selected from the control panel of the device.

Xylene was added to the cuvette and the outside walls of the cuvette were cleaned with a tissue paper, then placed in the spectrophotometer 208 (rinsing the cuvette walls was performed). The xylene measurement was used as the blank. A wavelength value was selected and the calibrate operation was selected. Blank calibrations were performed for each selected wavelength.

The cuvette was filled with the prepared crude oil solution and placed in the spectrophotometer 208 after the outside of the cuvette was rinsed. The absorbance was recorded, and the measurements were repeated at different wavelengths to cover the range of 320-1000 nm.

Figure 3:
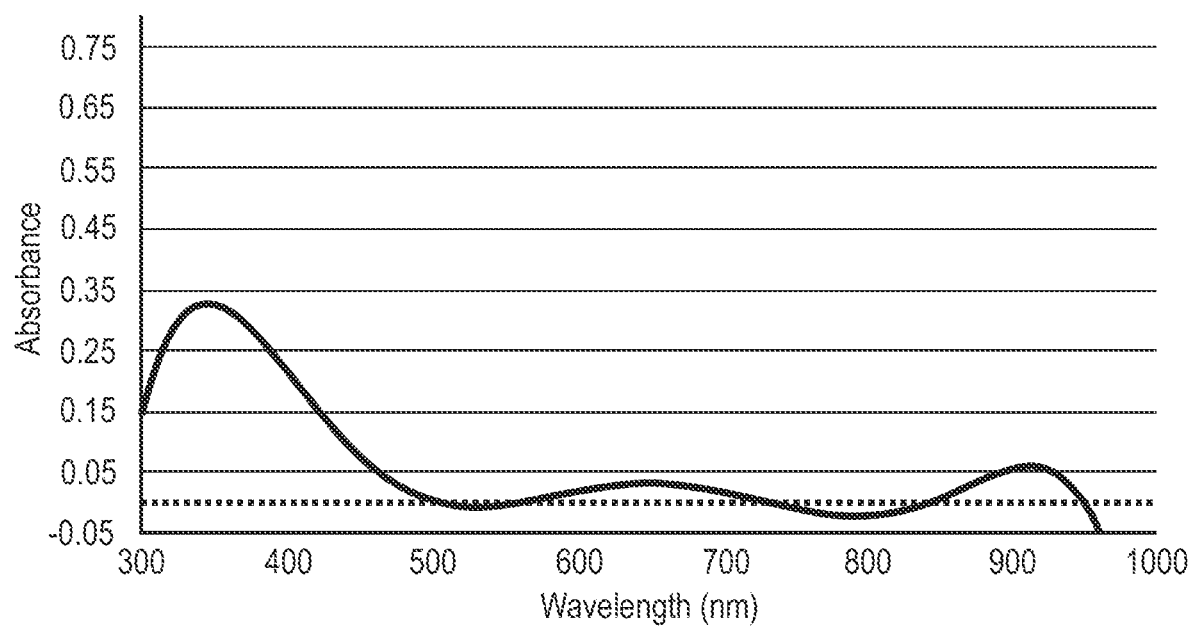
FIG. 3 is a polynomial interpolation of absorbance for a 100 ppm solution of a first crude oil in xylene.
Figure 4:
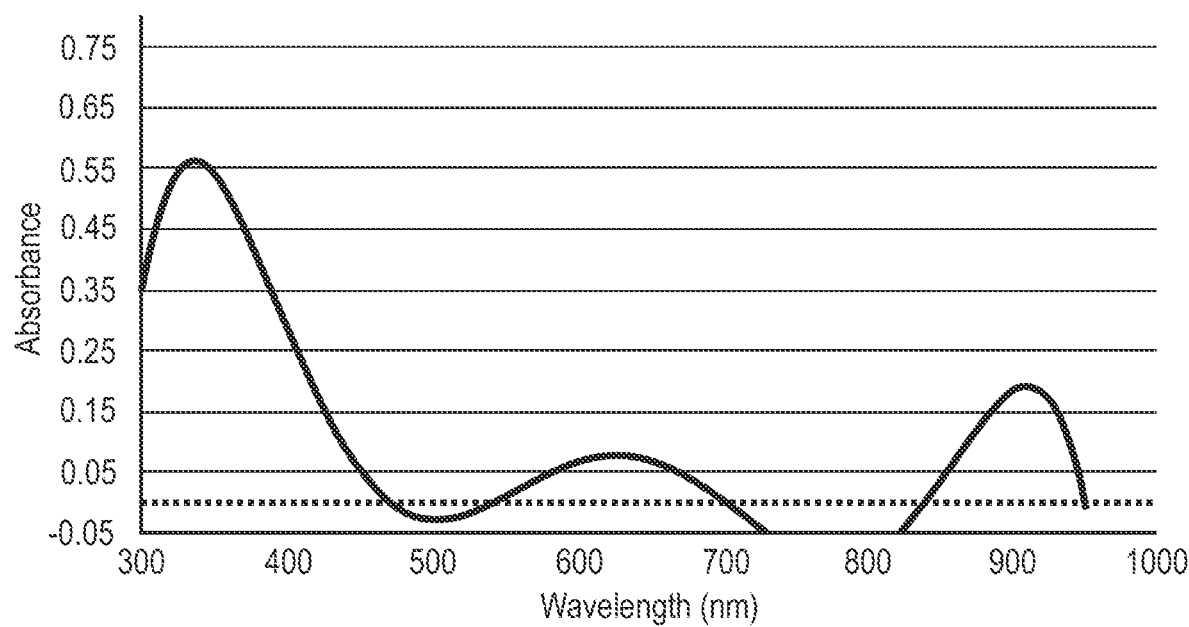
FIG. 4 is a polynomial interpolation of absorbance for a 100 ppm solution of a second crude oil in xylene.

A wavelength value was selected to have high relative absorbance. This will result in an external calibration line with a good repeatability, $r^2>0.995$, and substantially low percentage error, <10%. For example, 450 nm was chosen for crude oil A, which is near to the maximum absorbance wavelength, while 350 nm was chosen for crude oil B, which is the maximum absorbance wavelength. This is shown in FIGS. 3 and 4. FIG. 3 is a polynomial interpolation of absorbance for a 100 ppm solution of a first crude oil in xylene. FIG. 4 is a polynomial interpolation of absorbance for a 100 ppm solution of a second crude oil in xylene.

Calibration and measurement at 450 nm for crude oil A resulted in an $r^2=1$ and a % error of less than about −8.69%, while calibration and measurement at 350 nm for crude oil B resulted in an $r^2=0.9963$ and a % error of less than about −3.22%. The calibration curves are described further below.

Determine Calibration Curve

Figure 5:
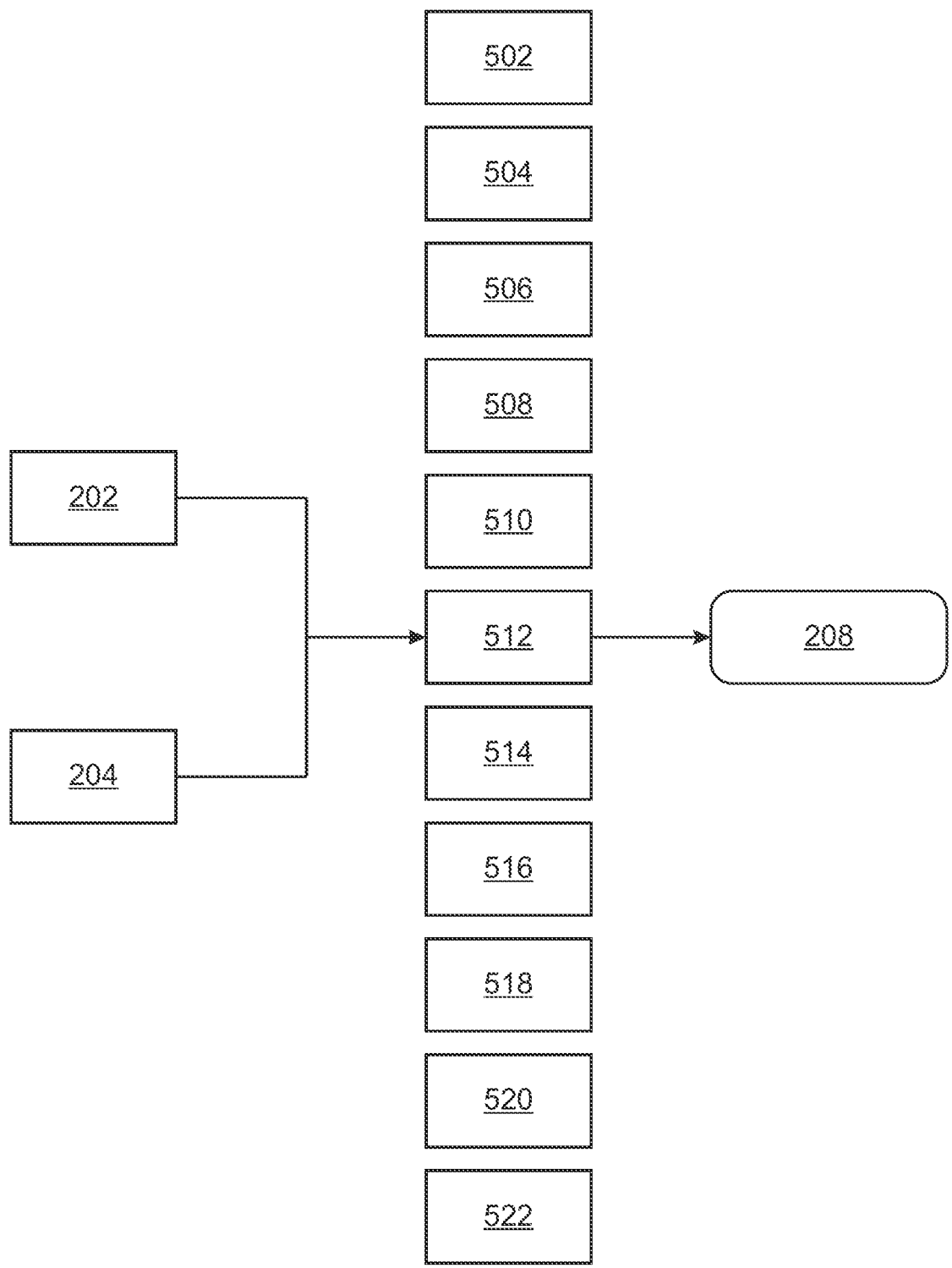
FIG. 5 is a schematic diagram of the calibration procedure.

FIG. 5 is a schematic diagram of the calibration procedure. This may correspond to blocks 104 and 106 of FIG. 1. Like numbered items are as described with respect to FIG. 2. In FIG. 5, the corresponding crude oil 202 was mixed with xylene 204 to form a series of calibration solutions, for example, at 10 ppm 502, 20 ppm 504, 40 ppm 506, 60 ppm 508, 80 ppm 510, 100 ppm 512, 200 ppm 514, 300 ppm 516, 400 ppm 518, 800 ppm 520, and 1000 ppm 522, among others. For example, 0.0001 g of the corresponding crude oil was added to a 10 mL volumetric flask and diluted to the mark with xylene. The flask was then shaken to prepare a 10 ppm solution (add 0.0002 g of crude oil instead of 0.0001 g for 20 ppm . . . etc.).

The specific concentration selected may depend on the expected concentration of the crude oil in water. The absorbance of each of the calibration solutions 502-522 are then measured at the selected wavelength in the spectrophotometer 208 as described with respect to the wavelength selection process. The calculations used to determine the concentrations are described below.

For example, a cuvette with xylene was placed in the instrument and the calibrate button was pressed. The cuvette was then filled with a prepared crude oil calibration solution and placed in the spectrophotometer (rinsing is recommended).

The absorbance of the solution was measured (3 repeated measurements for each calibration solution) and the results were recorded. The absorbance of the blank was checked after every 6 to 9 measurements to ensure it was at zero. The calibration results for the first crude oil sample (A) are shown in Table 1.

TABLE 1

Typical calibration measurements of crude oil A in xylene solutions

| Tube No. | Concentration (mg/L) | Absorbance at 450 nm | | | |
|---|---|---|---|---|---|
| | | Trial 1 | Trial 2 | Trial 3 | Average |
| 0 | 0.00 | 0.000 | 0.000 | 0.000 | 0.0000 |
| 1 | 10.10 | 0.005 | 0.006 | 0.005 | 0.0053 |
| 2 | 21.31 | 0.011 | 0.011 | 0.009 | 0.0103 |
| 3 | 45.37 | 0.022 | 0.021 | 0.021 | 0.0213 |
| 4 | 68.15 | 0.032 | 0.032 | 0.032 | 0.0320 |
| 5 | 93.66 | 0.046 | 0.044 | 0.044 | 0.0447 |
| 6 | 131.75 | 0.062 | 0.061 | 0.061 | 0.0613 |
| 7 | 269.13 | 0.125 | 0.124 | 0.126 | 0.1250 |
| 8 | 534.79 | 0.244 | 0.244 | 0.245 | 0.2443 |
| 9 | 799.91 | 0.370 | 0.369 | 0.370 | 0.3697 |
| 10 | 972.11 | 0.452 | 0.451 | 0.451 | 0.4513 |
| 11 | 1010.68 | 0.466 | 0.467 | 0.465 | 0.4660 |

Figure 6:
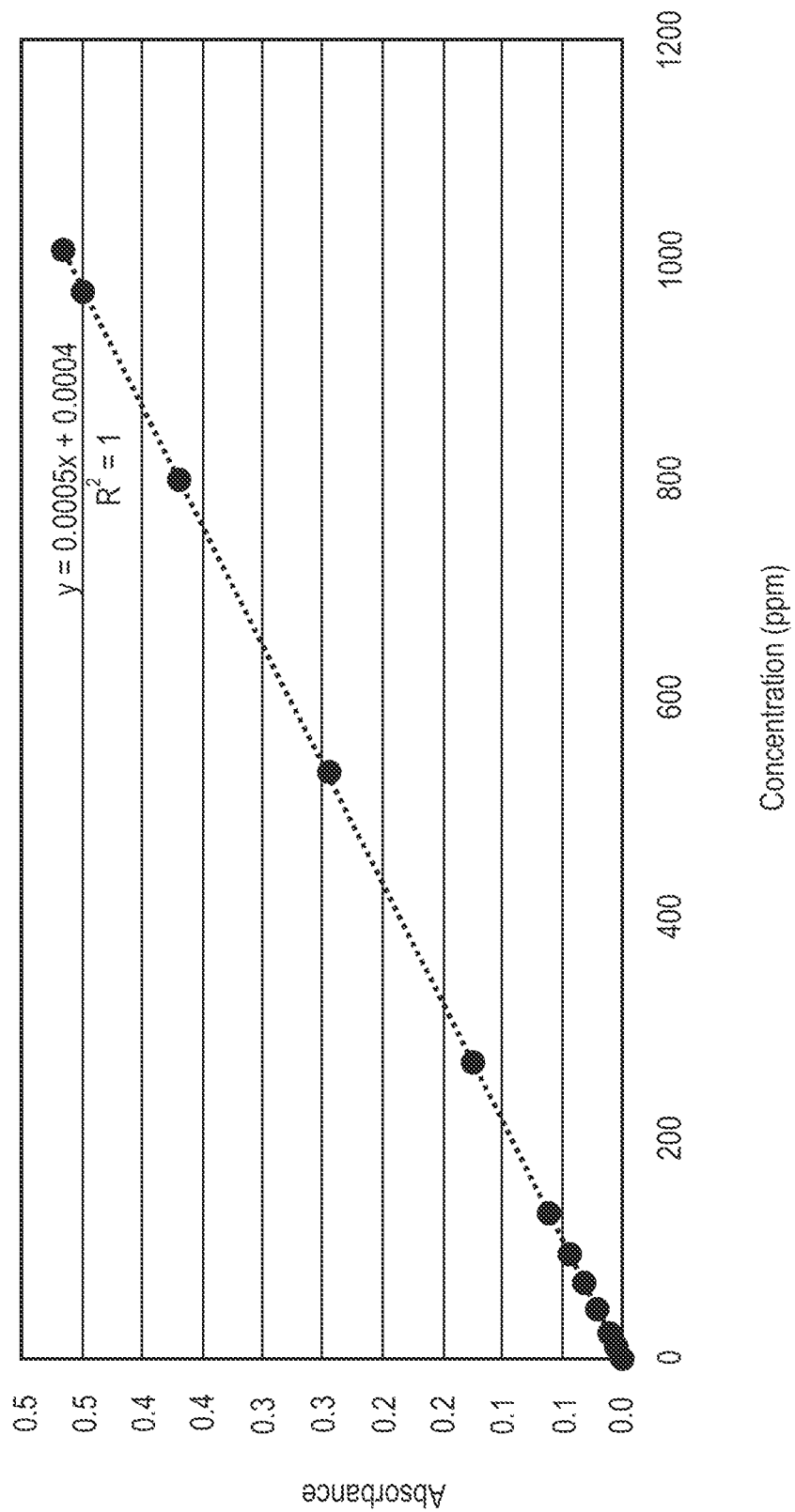
FIG. 6 is a plot of the calibration curve for the first crude oil.
Figure 7:
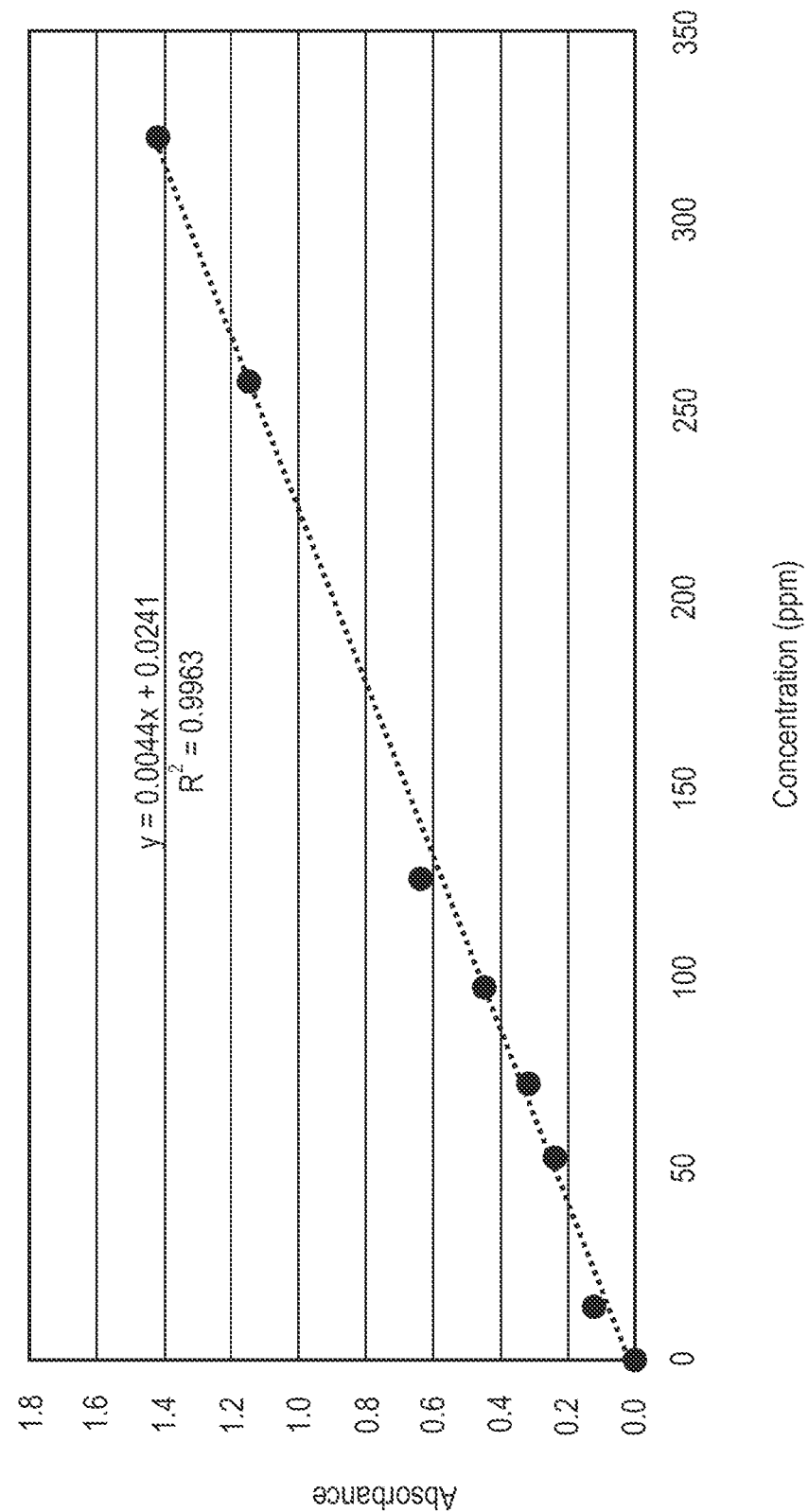
FIG. 7 is a plot of the calibration curve for the second crude oil.

The measured absorbances were plotted versus the concentrations, and a calibration line was constructed to find the equation of the line as shown in FIGS. 6 and 7. FIG. 6 is a plot of the calibration curve for the first crude oil. FIG. 7 is a plot of the calibration curve for the second crude oil. For both crude oils, it was confirmed that the $r^2$ is 0.995 or higher.

Sample Preparation and Measurement

Figure 8:
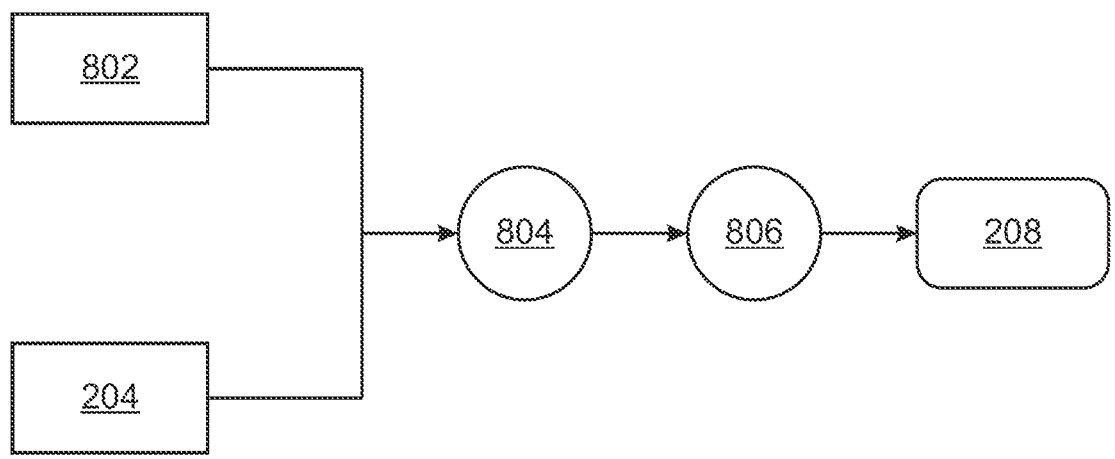
FIG. 8 is a schematic diagram of the sample preparation and measurement procedure.

FIG. 8 is a schematic diagram of the sample preparation and measurement procedure. This corresponds to blocks 108 and 110 of FIG. 1. Like numbered items are as described with respect to FIG. 2. After calibration, a water sample 802 was collected in a water sample bottle. The water sample bottle, including the water sample 802, was weighed and the total mass of the bottle was recorded. The water sample 802 was transferred to a separatory funnel 804 and the mass of the empty bottle was recorded to determine the mass of the water sample 802.

An appropriate amount of xylene 204 was added to the separatory funnel 804 and the amount of the added xylene 204 was recorded. Generally, the volume of the added xylene 204 depends on the amount of crude oil present in the water sample. However, the volume of the added xylene 204 generally equals about 10 vol. % to about 34 vol. % of the water sample 802.

The separatory funnel 804 was vigorously shaken, and the bottom, or water, layer was discarded. The top, or xylene, layer was transferred to a test tube. In some cases, the solution is diluted with additional xylene if the expected concentration is outside of the calibration range.

The test tube was placed in a centrifuge 806, and centrifuged for 5 minutes at 1500 rpm to remove water droplets and solids in the xylene layer. A pipet was used to transfer the xylene layer to the cuvette, avoiding the bottom of the test tube and the wall of the test tube, as the centrifugation pushed the water and solids down or to the side.

The cuvette was placed in the spectrophotometer 208, and the absorbance of the separated xylene layer was measured at the same wavelength used in the calibration. Three repeated measurements were run for each sample, and an average was calculated.

The concentration of total crude oil was then calculated from the recorded measurements using the equation shown in the calculation section below. Tables 2 and 3 show typical values and results for a sample of crude oil A in water.

For example, the mixture was transferred to a separatory funnel 804 for extraction with xylene 204, and processed in a centrifuge 806 to remove impurities.

Evaluation of Quality Control Data

Quality Control (QC)

QC samples are crude oil in brine mixtures that are treated as the samples. Using 3 QC samples of crude oil A in water containing 121.82 ppm, 422.76 ppm, and 890.28 ppm respectively, the relative error and the relative standard deviation for 10 replicate measurements of each (n=10) were found to be less than or equal to about −8.69% and less than or equal to about 1.9%, respectively.

Evaluation of Linearity

In addition to being used for the quantification, the calibration solutions were used to find the calibration line where the coefficient of determination ($r^2$) was greater than 0.995. As described herein, the absorbance curve for crude oil A, shown in FIG. 6, is linear in the provided range of concentrations (10-1000) with an $r^2$ of 1. Similarly, the absorbance curve for crude oil B, shown in FIG. 7, is linear with $r^2$=0.9963.

TABLE 2

Typical absorbance and concentration values of the separated xylene layer and the mass and volume of water in the water samples.

| Name | Absorbance values at 450 nm of the separated xylene layer | | | | Con. of total crude oil in xylene layer (mg/L) | Mass of full bottle, $m_f$ (g) | Mass of empty bottle, $m_e$ (g) | Mass of water, $m_w$ (g) = $m_f - m_e$ | Volume of water (mL) = density/$m_w$ |
|---|---|---|---|---|---|---|---|---|---|
| | Trial 1 | Trial 2 | Trial 3 | Average | | | | | |
| Sample 1 | 0.085 | 0.084 | 0.085 | 0.08467 | 168.54 | 571.4 | 243.2 | 328.2 | 328.851 |
| Sample 2 | 0.165 | 0.167 | 0.166 | 0.16600 | 331.20 | 568.1 | 243.2 | 324.9 | 325.545 |

TABLE 3

Typical total crude oil A concentrations in water and the mass and volume of the added xylene.

| Name | Mass of xylene, $m_{xyl}$ (g) | Volume of xylene (mL) = density/$m_{xyl}$ | Concentration of total crude oil A in water (mg/L) |
|---|---|---|---|
| Sample 1 | 24.900 | 28.953 | 14.84 |
| Sample 2 | 30.200 | 35.116 | 35.73 |

Preparation of Quality Control (QC) Samples

Quality control samples were prepared to determine the accuracy and precision of the method. To prepare the samples, 1 g of sodium chloride was added to a 50 mL volumetric flask and diluted to the mark with distilled water. The solution was shaken vigorously, resulting in a 2 wt. % NaCl solution (mass percentage).

3.749 g of calcium chloride dihydrate was added to a 50 mL volumetric flask, diluted to the mark with distilled water, and shaken vigorously. This prepared a 6 wt. % $CaCl_2$ solution (mass percentage).

The two prepared solutions were mixed, to prepare 100 mL of a 1 wt. % NaCl, 3 wt. % $CaCl_2$ brine solution. 0.001 g of the corresponding crude oil was added to a 10 mL volumetric flask, and diluted with the prepared brine to the mark and shaken. This prepared a 100 ppm mixture for the tests, although any concentration in the calibration range 10-1000 can be used.

The sample preparation and measurement procedure of FIG. 8 were used to measure and absorbance for the mixture.

Calculations

Concentrations of the Calibration Solutions the total crude oil concentration of each solution was determined using Equation 1 as follows:

$$C = \frac{m}{V_t} \qquad \text{Equation 1}$$

In Equation 1, C is the concentration of total crude oil in ppm, m is the mass of crude oil in mg, and $V_t$ is the total volume of the solution in L.

Calibration

The correlation between absorbance and the concentration of total crude oil was determined by linear regression from the external calibration samples, using Equation 2:

$$y = mx + c \qquad \text{Equation 2}$$

In equation 2, y is the absorbance with an arbitrary unit (absorbance units), m is the slope of the calibration line, x is the concentration of total crude oil in ppm, and c is the y-intercept.

Concentrations of the Samples

The concentration of total crude oil extracted from the water sample was determined using external calibration by rearranging Equation 2 as follows:

$$x = \frac{y - c}{m} \qquad \text{Equation 3}$$

Since the concentration value that was calculated from the absorbance measured in the device is the amount of the extracted crude oil in the added xylene, the concentration of total crude oil in water was determined by applying the following equation to account for LLE concentration change, according to Equations 4 and 5:

$$C_w V_w = C_{xyl} V_{xyl} \qquad \text{Equation 4}$$

$$C_w = \frac{C_{xyl} V_{xyl}}{V_w} \qquad \text{Equation 5}$$

In Equations 4 and 5, $C_w$ is the concentration of total crude oil in water in ppm, $V_w$ is the volume of water in mL, $C_{xyl}$ is the concentration of total crude oil in the added xylene in ppm, and $V_{xyl}$ is the volume of the added xylene in mL.

Example of Calculations

To calculate the concentration of a calibration solution given that: the mass of crude oil (m)=0.0001 g and the total volume ($V_t$)=10 mL. Using Equation 1, the concentration of total crude oil (C) is determined as follows:

$$C = \frac{m}{V_t} = \frac{0.0001 \text{ g}}{10 \text{ mL}} = \frac{0.1 \text{ mg}}{0.01 \text{ L}} = 10 \text{ ppm}$$

To calculate the concentration of total crude oil in the added xylene given that (from Table 2) the average absorbance (y)=0.08467, and (from FIG. 6), m=0.0005 and c=0.0004. Using Equation 3, the concentration of total crude oil in the added xylene (x) is determine as follows:

$$x = \frac{y - c}{m} = \frac{0.08467 - 0.0004}{0.0005} = 168.54 \text{ ppm}$$

To calculate the concentration of total crude oil in water given that the concentration of total crude oil in added xylene ($C_{xyl}$)=168.54 ppm, (from Table 3) the volume of added xylene ($V_{xyl}$)=28.953 mL, and (from Table 2) the volume of water ($V_w$)=328.851 mL. Using Equation 5, the concentration of total crude oil in water ($C_w$) is determine as follows:

$$C_w = \frac{C_{xyl} V_{xyl}}{V_w} = \frac{(168.54 \text{ ppm}) \times (28.953 \text{ mL})}{(328.851 \text{ mL})} = 14.84 \text{ ppm}$$

Performance Characteristics

The repeatability of the measurement expressed in relative standard deviation was determined by 10 replicate measurements (n=10) of a QC sample of 121.82 ppm. The relative standard deviation was ≤1.9%.

The measurement's uncertainty was determined based on 10 replicate measurements (n=10) of the QC sample using the following equation:

$$C_k = C_m \pm t_{(n-1)} \times \frac{s}{\sqrt{n}} \qquad \text{Equation 6}$$

In Equation 6, $C_k$ is the concentration of the QC sample, $C_m$ is the mean of the actual concentration, t is the value of the tabulated t-test at (n−1) replicates at 95% confidence interval, s is the estimated standard deviation, and n is the number of replicates. The uncertainty is determined using Equation 7:

$$\text{uncertainty} = \pm t_{(n-1)} \times \frac{s}{\sqrt{n}} \qquad \text{Equation 7}$$

$$\text{uncertainty} = \pm 2.26 \times \frac{2.094}{\sqrt{10}} = \pm 1.497 \text{ ppm}$$

The relative uncertainty was found to be ±0.0137, and the relative error and relative standard deviation were reported as described with respect to the quality control data.

Reporting of Results

An average of three measurement for the concentration of total crude oil in water were reported in parts per million (mg/L) up to two decimal points. The coefficients of determination ($r^2$) for multiple trials of calibrations were high, ranging from 0.999 to 1, indicating a high correlation between the response and the concentrations of the prepared solutions.

The prepared quality control samples showed that the method has a relative error ≤−8.69%. The method had repeatability expressed as relative standard deviation with the value of ≤1.9%. The method had relative uncertainty equal to ±0.0137.

Embodiments

An embodiment described in examples herein provides a method for quantifying a crude oil in water. The method includes selecting an ultraviolet/visible (UV/Vis) wavelength to perform a measurement, preparing calibration solutions in xylene, and preparing a calibration curve from the calibration solutions. A sample is prepared including extracting the crude oil from the water in a \ separation with xylene. An absorbance of the sample in the xylene is measured at the UV/Vis wavelength. A concentration of the crude oil in the water is calculated from the absorbance.

In an aspect, selecting the UV/Vis wavelength includes dissolving a 100 ppm sample of the crude oil in xylene to form a test solution, measuring a UV/Vis absorbance spectrum of the test solution, and selecting a wavelength in the UV/Vis absorbance spectrum at or near a maximum absorbance.

In an aspect, preparing the calibration solutions includes preparing a series of crude oil solutions in xylene at concentrations between about 10 ppm and about 1000 ppm. In an aspect, preparing the calibration curve includes obtaining three measurements of an absorbance of each calibration solution in the series of crude oil samples at the UV/Vis wavelength, averaging the three measurements of each calibration solution to obtain an average absorbance value for that calibration solution, plotting the average absorbance value for each calibration solution against the concentration of that calibration solution, and performing a linear regression to obtain a calibration equation. In an aspect, the method includes determining that the coefficient of determination ($r^2$) of the calibration equation is at least 0.995.

In an aspect, preparing the sample includes adding a water sample to a separatory funnel, adding the xylene to the separatory funnel, shaking the separatory funnel, extracting a xylene layer, and centrifuging the xylene layer.

In an aspect, measuring the absorbance includes placing the xylene layer in a cuvette after centrifugation, obtaining three measurements of the absorbance of the xylene layer, and calculating the concentration of crude oil in the xylene layer.

In an aspect, calculating the concentration of the crude oil in the water by normalizing the concentration of the crude oil in the xylene layer by the volume of the xylene versus the volume of the water, using the equation:

$$C_w = \frac{C_{xyl} V_{xyl}}{V_w},$$

wherein $C_w$ is the concentration of total crude oil in water in ppm, $V_w$ is the volume of water in mL, $C_{xyl}$ is the concentration of total crude oil in the added xylene in ppm, and $V_{xyl}$ is the volume of the added xylene in mL.

In an aspect, the method includes preparing quality control samples by preparing a synthetic brine and mixing a known amount of the crude oil with the synthetic brine. In an aspect, the method includes measuring the amount of the crude oil in the synthetic brine by extracting the crude oil from the synthetic brine using xylene in a liquid-liquid extraction, removing a xylene layer from the liquid-liquid extraction, centrifuging the xylene layer, measuring the absorbance of the xylene layer, and calculating the concentration of the crude oil in the synthetic brine from the absorbance of the xylene layer. In an aspect, the method includes repeating the measurement of the concentration of the crude oil in the synthetic brine for 10 measurements, and determining an error for the measurement.

Other implementations are also within the scope of the following claims.

What is claimed is:

1. A method for quantifying a crude oil in water, comprising:
    selecting an ultraviolet/visible (UV/Vis) wavelength to perform a measurement;
    preparing calibration solutions in xylene;
    preparing a calibration curve from the calibration solutions;
    preparing a sample comprising extracting the crude oil from the water in a two-phase separation with xylene;
    measuring an absorbance of the sample in the xylene at the UV/Vis wavelength; and
    calculating a concentration of the crude oil in the water from the absorbance.

2. The method of claim 1, wherein selecting the UV/Vis wavelength comprises:
    dissolving a 100 ppm sample of the crude oil in xylene to form a test solution;
    measuring a UV/Vis absorbance spectrum of the test solution; and
    selecting a wavelength in the UV/Vis absorbance spectrum at or near a maximum absorbance.

3. The method of claim 1, wherein preparing the calibration solutions comprises preparing a series of crude oil solutions in xylene at concentrations between about 10 ppm and about 1000 ppm.

4. The method of claim 3, wherein preparing the calibration curve comprises:
    obtaining three measurements of an absorbance of each calibration solution in the series of crude oil samples at the UV/Vis wavelength;
    averaging the three measurements of each calibration solution to obtain an average absorbance value for that calibration solution;
    plotting the average absorbance value for each calibration solution against the concentration of that calibration solution; and
    performing a linear regression to obtain a calibration equation.

5. The method of claim 4, comprising determining that the coefficient of determination ($r^2$) of the calibration equation is at least 0.995.

6. The method of claim 1, wherein preparing the sample comprises:
    adding a water sample to a separatory funnel;
    adding the xylene to the separatory funnel;
    shaking the separatory funnel;
    extracting a xylene layer; and
    centrifuging the xylene layer.

7. The method of claim 6, wherein measuring the absorbance comprises:
    placing the xylene layer in a cuvette after centrifugation;
    obtaining three measurements of the absorbance of the xylene layer; and
    calculating the concentration of crude oil in the xylene layer.

8. The method of claim 7, comprising calculating the concentration of the crude oil in the water by normalizing the concentration of the crude oil in the xylene layer by the volume of the xylene versus the volume of the water, using the equation:

$$C_w = \frac{C_{xyl} V_{xyl}}{V_w},$$

wherein $C_w$ is the concentration of total crude oil in water in ppm, $V_w$ is the volume of water in mL, $C_{xyl}$ is the concentration of total crude oil in the added xylene in ppm, and $V_{xyl}$ is the volume of the added xylene in mL.

9. The method of claim 1, comprising preparing quality control samples by:
    preparing a synthetic brine; and
    mixing a known amount of the crude oil with the synthetic brine.

10. The method of claim 9, comprising measuring the amount of the crude oil in the synthetic brine by:
    extracting the crude oil from the synthetic brine using xylene in a liquid-liquid extraction;
    removing a xylene layer from the liquid-liquid extraction;
    centrifuging the xylene layer;
    measuring the absorbance of the xylene layer; and
    calculating the concentration of the crude oil in the synthetic brine from the absorbance of the xylene layer.

11. The method of claim 10, comprising;
    repeating the measurement of the concentration of the crude oil in the synthetic brine for 10 measurements; and
    determining an error for the measurement.

* * * * *